(12) United States Patent
Shimazu et al.

(10) Patent No.: US 11,786,189 B2
(45) Date of Patent: Oct. 17, 2023

(54) PROXIMITY OPERATION-TYPE X-RAY FLUOROSCOPIC IMAGING APPARATUS

(71) Applicant: SHIMADZU CORPORATION, Kyoto (JP)

(72) Inventors: Keisuke Shimazu, Kyoto (JP); Takayoshi Okamura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 95 days.

(21) Appl. No.: 17/531,794

(22) Filed: Nov. 21, 2021

(65) Prior Publication Data

US 2023/0157651 A1 May 25, 2023

(51) Int. Cl.
*A61B 6/10* (2006.01)
*A61B 6/04* (2006.01)
*A61B 6/00* (2006.01)

(52) U.S. Cl.
CPC .......... *A61B 6/107* (2013.01); *A61B 6/0407* (2013.01); *A61B 6/0487* (2020.08); *A61B 6/4429* (2013.01); *A61B 6/487* (2013.01)

(58) Field of Classification Search
CPC ..... A61B 6/107; A61B 6/0407; A61B 6/0487; A61B 6/4429; A61B 6/4435; A61B 6/447; A61B 6/485; A61B 6/487
See application file for complete search history.

(56) References Cited

U.S. PATENT DOCUMENTS

| | | | | |
|---|---|---|---|---|
| 3,280,331 A * | 10/1966 | Abt | ........................... | G21F 3/00 976/DIG. 335 |
| 4,062,518 A * | 12/1977 | Stivender | ............... | A61B 6/107 976/DIG. 335 |
| 6,278,125 B1 * | 8/2001 | Belek | ........................ | G21F 3/00 250/519.1 |
| 7,331,712 B2 * | 2/2008 | Fischer | ................ | A61B 6/4464 250/519.1 |
| 9,867,583 B1 * | 1/2018 | Colling | .................. | A61B 6/107 |
| 9,953,731 B2 * | 4/2018 | Buchmeyer | ............... | G21F 3/00 |
| 11,006,909 B2 * | 5/2021 | Yifat | .......................... | G21F 3/00 |
| 2008/0149864 A1 * | 6/2008 | Hargrove | .................. | G21F 3/00 29/428 |
| 2012/0241652 A1 * | 9/2012 | Jeschke | .................. | A61B 6/107 250/519.1 |

(Continued)

FOREIGN PATENT DOCUMENTS

JP 2008-61765 A 3/2008
JP 2010-240010 A 10/2010

*Primary Examiner* — Dani Fox
*Assistant Examiner* — Soorena Kefayati
(74) *Attorney, Agent, or Firm* — Andrew F. Young; NOLTE LACKENBACH SIEGEL

(57) ABSTRACT

An X-ray shielding unit 19 includes a plurality of shielding slats, freely movable with an imaging system that is in place above a table, and each free end of the shielding slats extends toward the table and is the slats are arrayed in parallel along the long side of the table. A shielding switching element switches the X-ray shielding unit between a shielding state in which the X-ray exposure to the operator S is blocked and a releasing state. The shielding switching element includes a slat rotation mechanism rotating respective shielding slats on a short side axis of the table, and the slat rotation mechanism rotates the shielding slats during switching of the shielding state.

2 Claims, 10 Drawing Sheets

(56) References Cited

U.S. PATENT DOCUMENTS

| | | | | |
|---|---|---|---|---|
| 2013/0112899 A1* | 5/2013 | Schulz | .................... | E06B 5/18 |
| | | | | 250/517.1 |
| 2015/0272519 A1* | 10/2015 | Buchmeyer | .............. | A61N 5/10 |
| | | | | 250/515.1 |
| 2016/0336085 A1* | 11/2016 | Buchmeyer | ............ | A61B 6/107 |
| 2017/0119324 A1* | 5/2017 | Wilson | .................. | A61G 13/10 |
| 2017/0301424 A1* | 10/2017 | Thomas | ................. | A61B 6/107 |
| 2019/0142353 A1* | 5/2019 | Stegehuis | .............. | A61B 6/107 |
| | | | | 250/515.1 |

* cited by examiner

PROXIMITY OPERATION-TYPE X-RAY FLUOROSCOPIC IMAGING APPARATUS

CROSS REFERENCE TO RELATED APPLICATIONS

This application relates to, and but does not claim priority from, Ser. No.: JP 2019-114042 filed Jun. 19, 2019, published as JP 2021-154A on Jan. 7, 2021, the entire contents of which are incorporated herein by reference.

FIGURE SELECTED FOR PUBLICATION

FIG. 6.

BACKGROUND OF THE INVENTION

Field of the Invention

The present invention relates to a proximity operation-type (operative) X-ray imaging apparatus, and particularly, relates to an X-ray fluoroscopic imaging apparatus having an X-ray shielding mechanism to reduce an X-ray exposed dose for an operator.

Background

Conventionally, the proximity operative X-ray fluoroscopic imaging apparatus is applied to a contrast radiography for a digestive tract using barium. Relative to the proximity operative X-ray fluoroscopic imaging apparatus, the operator stands by the X-ray fluoroscopic imaging apparatus, instructs a subject, conducts an operation of an X-ray imaging system and a tilting operation of a table. The X-ray imaging system comprises an X-ray tube that irradiates X-ray and an X-ray detector that detects such X-rays. With regard to the proximity operative X-ray fluoroscopic imaging apparatus, in general, an under-table tube type X-ray fluoroscopic imaging platform in which the X-ray tube positions beneath the table on which the subject is loaded and the X-ray detector positions above the table is applied (e.g., refer to Patent Document 1).

The proximity operative X-ray fluoroscopic imaging apparatus enables to reduce the anxiety of the subject and provide promptly and adequately the subject with an instruction, so that it can be more advantageous than the remote operation model with regard to such points. On the other hand, with regard to the proximity operative X-ray fluoroscopic imaging apparatus, the configuration thereof having an X-ray shielding mechanism to lower the X-ray exposed dose for the operator who positions in the proximity of the X-ray apparatus is proposed (e.g., referring to Patent Document 2). The traditional X-ray shielding mechanism has a sheet-like shielding material made of such as lead. Such a sheet-like shielding material shields the space between the operator, who is in the proximity of the table, and the X-ray imaging apparatus, so that the exposed dose against the operator can be lowered.

RELATED PRIOR ART

Patent Documents

Patent Document 1-JP 2010-240010 A1
Patent Document 2-JP 2008-061765 A1

ASPECTS AND SUMMARY OF THE INVENTION

Objects to be Solved

Nevertheless, in the case of a conventional example having such structure, following problems are remained to be solved.

For example, one shielding material for the X-ray shielding mechanism has a weight in between 5 kg and 10 kg, so that in some case, the shielding material may be deformed due to the own weight when installing vertically. Accordingly, the X-ray shielding mechanism is installed so as to connect with the X-ray detector installed above the table, and the shielding material hangs downwardly from the X-ray detector over the table to prevent the deformation of the shielding material due to the own weight.

Here, such a shielding mechanism to block the operator view depending on a kind of operation may not be required, so that the X-ray shielding mechanism of the conventional X-ray fluoroscopic imaging apparatus is configured to be arbitrary removable. However, when such a heavy X-ray shielding mechanism is removed, the weight balance of the X-ray imaging system with the counterweight is changed. It is problematic that the operability of the X-ray imaging apparatus worsens when the weight balance of the X-ray imaging system is changed.

One measures to avoid such an effect can be the method wherein a dummy weight replacing the X-ray shielding mechanism is connected with the X-ray detector when the X-ray shielding mechanism is removed. However, the measures for the X-ray shielding mechanism using the dummy weight needs an action to change the X-ray shielding mechanism to the dummy weight, so that a workload on the operator becomes larger and the time needed for the X-ray fluoroscopic imaging becomes longer. In addition, it can be problematic to find the storage space for the X-ray shielding mechanism or the dummy weight not in use must be ensured.

Considering such circumstances, the object of the present invention is to provide an X-ray fluoroscopic imaging apparatus capable of reducing the workload on the operator and lowering the radiation exposed dose for the operator.

According to one alternative aspect of the present invention, there is provided an X-ray proximity operative fluoroscopic imaging apparatus capable of reducing the workload on the operator and lowering the radiation dose for the operator. The X-ray shielding unit comprises a plurality of shielding slats. Each pedestal end of the shielding slats is supported so as to be freely movable with the imaging system that is in place above the table, and each free end of the shielding slats is extending toward a loading surface of the table. A plurality of the shielding slats are arrayed in parallel along the long side direction to table. The shielding switching element switches the X-ray shielding unit between the shielding state in which the X-ray exposure to the operator S is blocked and the releasing state in which the shielding state is released. The shielding switching element comprises the slat rotation mechanism that rotates the respective shielding slats around the short side direction axis of the table, and the slat rotation mechanism rotates the shielding slats so that the shielding state and the releasing state can be switched.

Means for Solving the Problem

The present invention constitutes the following structure to solve such problems.

Specifically, a proximity operative X-ray fluoroscopy and imaging apparatus of the present invention comprises: a table on which a subject is held; an imaging system in which an X-ray tube that irradiates X-ray and an X-ray detector that detects the X-ray irradiated therefrom and transmitting the subject are facing each other while sandwiching the table; a table driving element that tilts the table relative to the horizontal plane; an X-ray shielding mechanism having a plurality of X-ray shielding slats, wherein each pedestal end of said shielding slats is supported so as to be freely movable with said imaging system that is in place above said table, each free end of said shielding slats is extending toward a loading surface of said table, and said plurality of said shielding slats are arrayed in parallel along a long side of said table; and a shielding switching element that switches a shielding state, in which said X-ray shielding mechanism is in place between said subject and an operator to shield an X-ray exposed dose for said operator, and a releasing state, in which said shielding is being released; a release state in which the shielding is released; wherein the shielding switching element further comprises: a slat rotation element that rotates the respective shielding slats around the short side axis of the table, wherein the shielding state and the release state are switched by that the slat rotation element rotates respective X-ray shielding slats.

According to such a configuration, the X-ray shielding mechanism can be switched from the shielding state to the releasing state without taking the X-ray shielding mechanism having the X-ray shielding slats off the proximity operative X-ray fluoroscopic imaging apparatus. Accordingly, the weight balance of the imaging system would not change even when the X-ray shielding mechanism is switched to the releasing state, so that the incident of lowering the operability of the proximity operative X-ray fluoroscopic imaging apparatus can be prevented. In addition, the action to connect the dummy weight with the imaging system when the shielding state and the releasing state are switched is not needed, so that the workload on the operator lowers and the convenience of the proximity operative X-ray fluoroscopic imaging apparatus can be improved.

According to the present invention set forth above, it is preferable that the slat rotation element changes the rotation angle of the X-ray shielding slats corresponding to the angle generated when the table driving element tilts the table.

Action and Effect

The proximity operative X-ray fluoroscopic imaging apparatus according to the present invention enables to rotate arbitrary the X-ray shielding slats corresponding to the tilt angle of the table when the table driving element tilts the table relative to the horizontal plane. Accordingly, an incident of deformation of the X-ray shielding slats due to the own weight of the X-ray shielding mechanism can be avoided.

According to the present invention set forth above, it is preferable that the slat rotation element switches between the shielding state to the releasing state by rotating respective X-ray shielding slats so that the traveling direction of the free end of the X-ray shielding slats becomes in parallel to the long side direction of the table.

Action and Effect

The proximity operative X-ray fluoroscopic imaging apparatus according to the present invention makes the X-ray shielding plane of the X-ray shielding mechanism further narrow when changed to the releasing state. Accordingly, the operator sight for such as the loading plane of the table can be ensured more adequately when the X-ray shielding mechanism is switched to the releasing state.

Effects of the Present Invention

The proximity operative X-ray fluoroscopic imaging apparatus according to the present invention can switch the X-ray shielding mechanism from the shielding state to the releasing state without taking the X-ray shielding mechanism having the X-ray shielding slats off the proximity operative X-ray fluoroscopic imaging apparatus. Accordingly, the weight balance of the imaging system would not change even when the X-ray shielding mechanism is switched to the releasing state, so that the incident of lowering the operability of the proximity operative X-ray fluoroscopic imaging apparatus can be avoided. In addition, the action to connect the dummy weight with the imaging system when the shielding state and the releasing state are switched is not needed, so that the workload on the operator lowers and the convenience of the proximity operative X-ray fluoroscopic imaging apparatus can be improved.

DETAILED DESCRIPTION OF THE PREFERRED EMBODIMENTS

Figure 1:
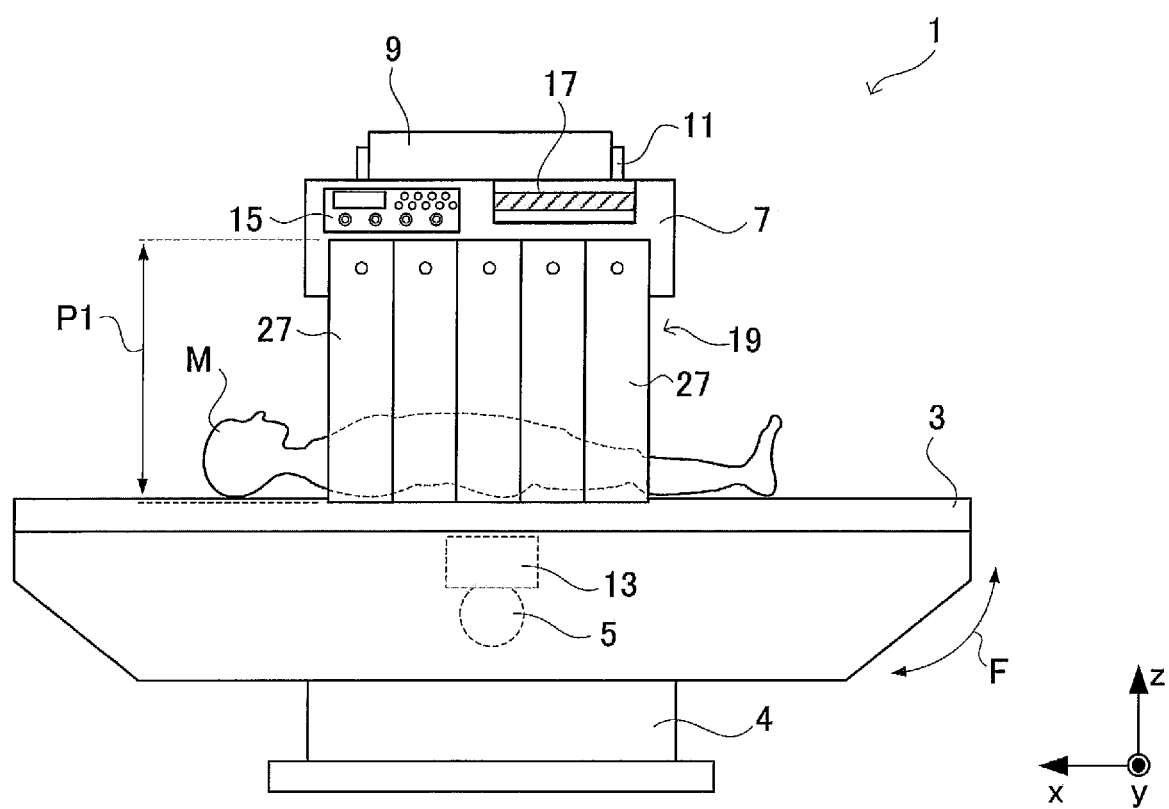
FIG. 1 is a front view illustrating the schematic structure of a proximity operative X-ray fluoroscopic imaging apparatus according to the Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements, modules or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors, resistors, capacitors, switches, and any other electronic-circuit-related elements, and any combinations of these structures etc. as will be understood by those of skill in the art as also being identified as or capable of operating the systems and devices and subcomponents noted herein and structures that accomplish the functions without restrictive language or label requirements since those of skill in the art are well versed in related devices, computer and operational controls and technologies of radiographic devices and all their sub components, elements, modules, and programs, including various circuits, elements, and modules, and combinations thereof without departing from the scope and spirit of the present invention.

Referring to FIGs, the inventors set forth the Embodiment of the present invention.

Illustration of the Entire Structure

Referring to FIG. 1, the proximity operative X-ray fluoroscopic imaging apparatus 1 according to the Embodiment comprises a table 3 on which a subject M is loaded. The table 3 is supported with a base 4 installed to a floor surface and is configured to be rotatable around a y-direction (the short side direction of the table 3).

An X-ray tube 5 that irradiates the subject M with X-ray is in place beneath the table 3. An X-ray detection unit 7 is in place above the table 3 to face the X-ray tube 5. The X-ray detection unit 7 embeds an X-ray detector 8 that detects the X-ray irradiated from the X-ray tube 5 and outputs an X-ray detection signal. The X-ray detector 8 are in-place facing the X-ray tube 5 while sandwiching the table 3. Examples of the X-ray detector 8 are such as a flat panel detector (FPD) and an image intensifier.

Figure 2:
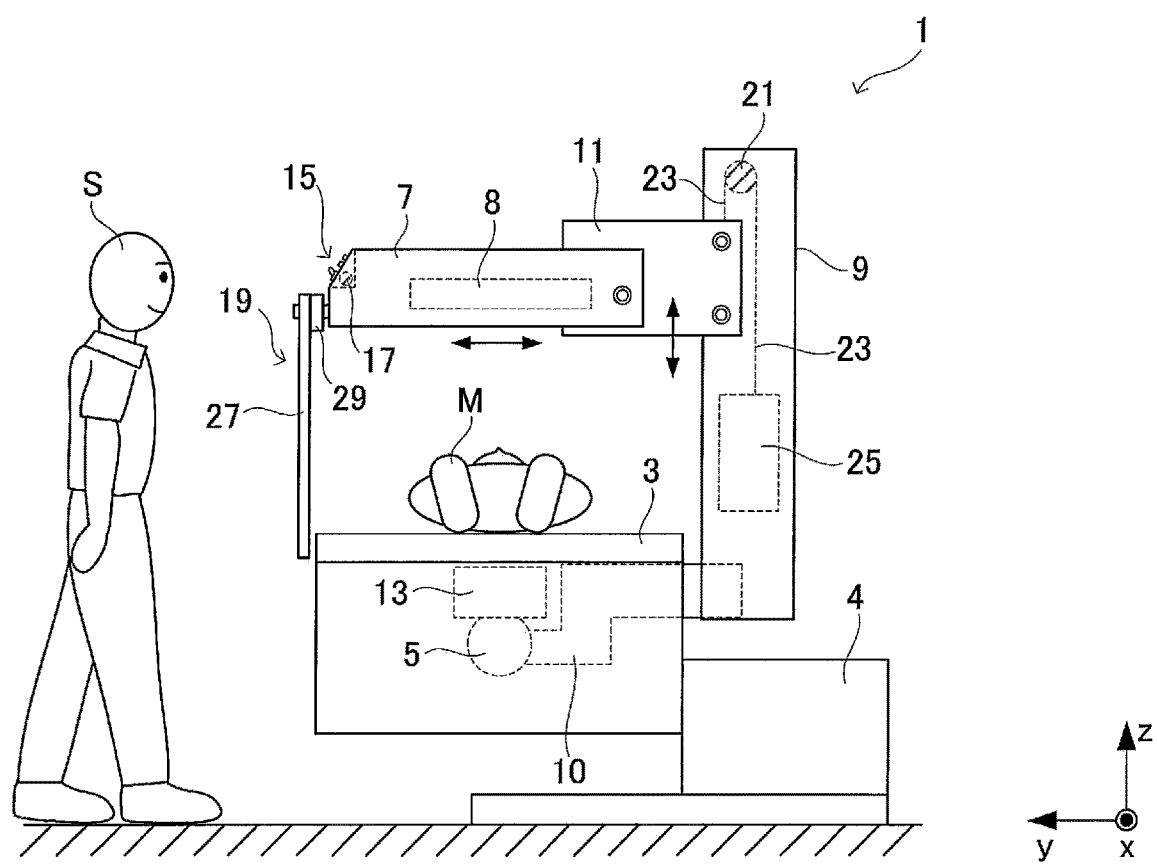
FIG. 2 is a right-side view illustrating the schematic structure of a proximity operative X-ray fluoroscopic imaging apparatus according to the Embodiment.

An X-ray fluoroscopic imaging apparatus 1 comprises a support column 9. Referring to FIG. 2, a pedestal portion of the support column 9 is connected with the table 3 through a connection element 10 and the support column 9 is extending in the intersecting direction with the table 3. The support column 9 is guided by a guide rail, which is not shown in FIG. and installed to the table 3 and configured to be movable in the long side direction of the table 3. In addition, the support column 9 can be directly connected with the table 3 or indirectly connected therewith through a member different from the connection element 10.

One end of a brunch element 11 extending in the short side direction of the table 3 is fixed on the support column 9. The brunch element 11 is movable up and down along the support column 9 and the other end of the brunch element 11 is connected with the X-ray detection unit 7. The X-ray detection unit 7 is guided by a guide rail, which is not shown in FIG and installed to the brunch element 11, and movable in the short side direction of the table 3.

In addition, the connection element 10 is connected with the support column 9 and also connected with the X-ray tube 5. And the connection element 10 is guided by the guide rail embedded in the table 3 and the support column 9 and movable in the short direction of the table 3 in synchronism with the X-ray detection unit 7.

Specifically, the imaging system comprises the X-ray tube 5 and the X-ray detector 8 which are connected to each other through the table 3, the support column 9, the connection element 10 and the brunch element 11 and movable in synchronism with each other in both long side and short side of the table 3. In addition, when the table 3 rotates, the X-ray tube and the X-ray detection unit 7 rotates along with the table 3 in a unified manner.

The X-ray tube 5 comprises a collimator 13. The collimator 13 limits X-rays irradiated from the X-ray tube 5 to a predetermined shape. An example of the predetermined shape is a cone shape like a pyramid.

Referring to FIG. 1 and FIG. 2, an operation panel 15 and an operation grip 17 are installed to the tip portion of the X-ray detection unit 7. The operation panel 15 comprises an operation device to set up an X-ray irradiation condition or an operation device for X-ray imaging and so forth, and the operator can input an instruction as to the X-ray fluoroscopic imaging by operating the operation panel 15. The operation panel 15 is such as a touch panel, a switch for switching over, and a switch using a push button.

The operation grip 17 comprises a power assist unit (not shown in FIG.). The operator holds the operation grip 17 to move e.g., the X-ray detection unit 7 in the long side direction and short side direction of table 3 and an orthogonal direction thereto. The operation panel 15 and the operation grip 17 can be in place anywhere the operator can easily operate and accordingly, the installation position is not limited to the tip portion of the X-ray detection unit 7.

An X-ray shielding unit 19 is in place to the tip portion of the X-ray detection unit 7. The X-ray shielding unit 19 cuts the exposed dose for the operator with X-ray irradiated from the X-ray tube 5 and is in place between the operator S, who works on a variety of jobs in the proximity of the X-ray fluoroscopic imaging apparatus 1, and the table 3.

Referring to FIG. 2, a pulley 21, a wire 23 and a counterweight 25 are embedded in the support column 9. The pulley 21, which is embedded in the top end of the support column 9, is hung with the wire 23. One end of the wire 23 is fixed on the branch element 11 and the other end of the wire 23 is fixed on the counterweight 25. The weight of the counterweight 25 is designed to balance with the total weight of the branch element 11, the X-ray detection unit 7 and the X-ray shielding unit 19.

The pulley 21 is rotatable in both clockwise (forward) and counterclockwise (reverse) directions and the wire 23 is movable in both direction while interlocked with rotation of the pulley 21. And the branch element 11 connected with the wire 23 is movable up and down along the support column 9 while interlocked with the wire 23. For example, given the pulley 21 rotates in the clockwise direction as shown in FIG. 2, the branch element 11 moves upward along the support column 9.

Structure of the X-Ray Shielding Unit

Figure 3:
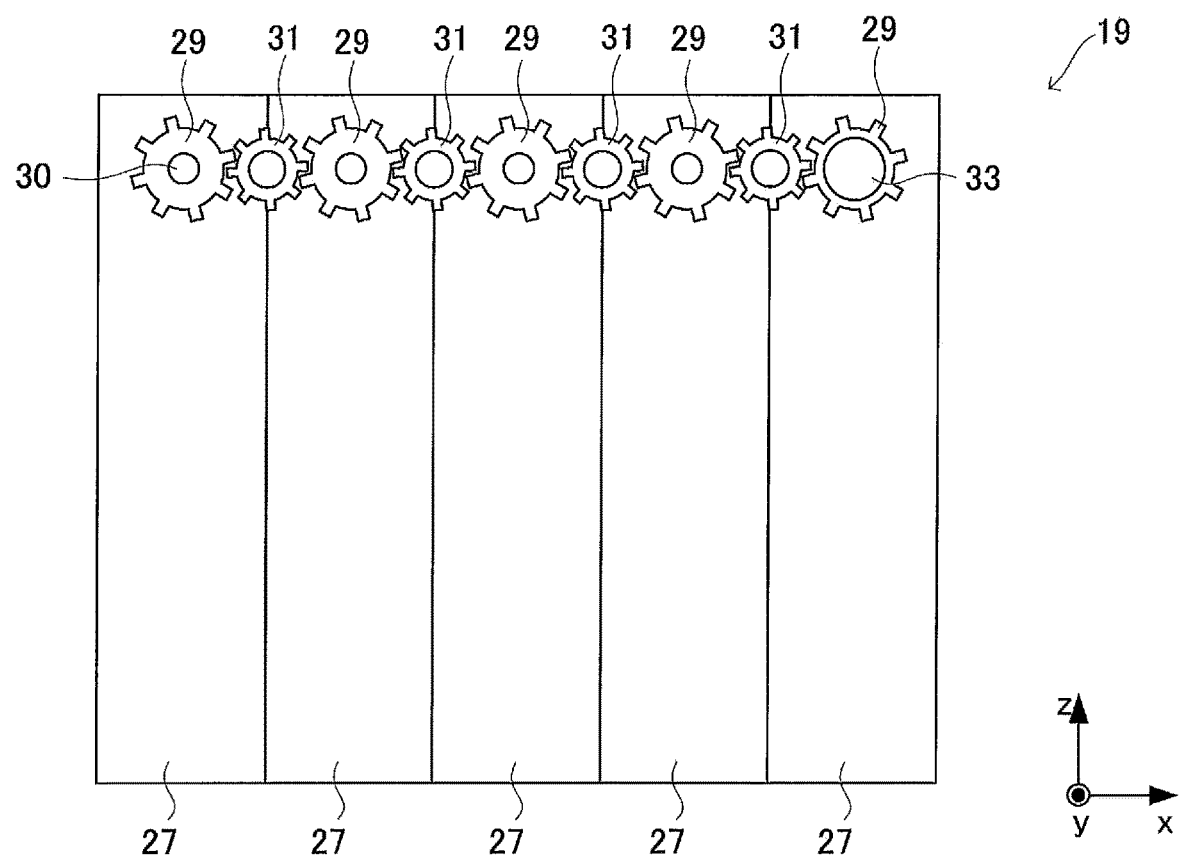
FIG. 3 is a back view illustrating a unit structure of the X-ray shielding unit according to the Embodiment.
Figure 4:
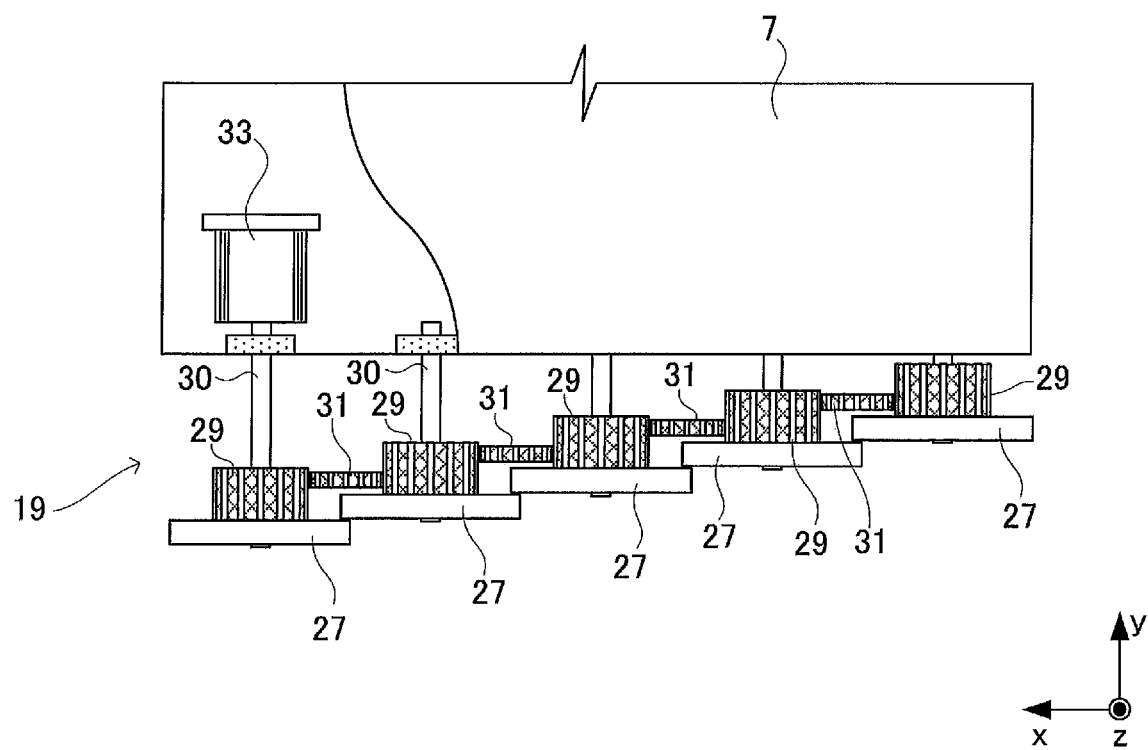
FIG. 4 is a plan view illustrating the unit structure of the X-ray shielding unit according to the Embodiment.
Figure 5:
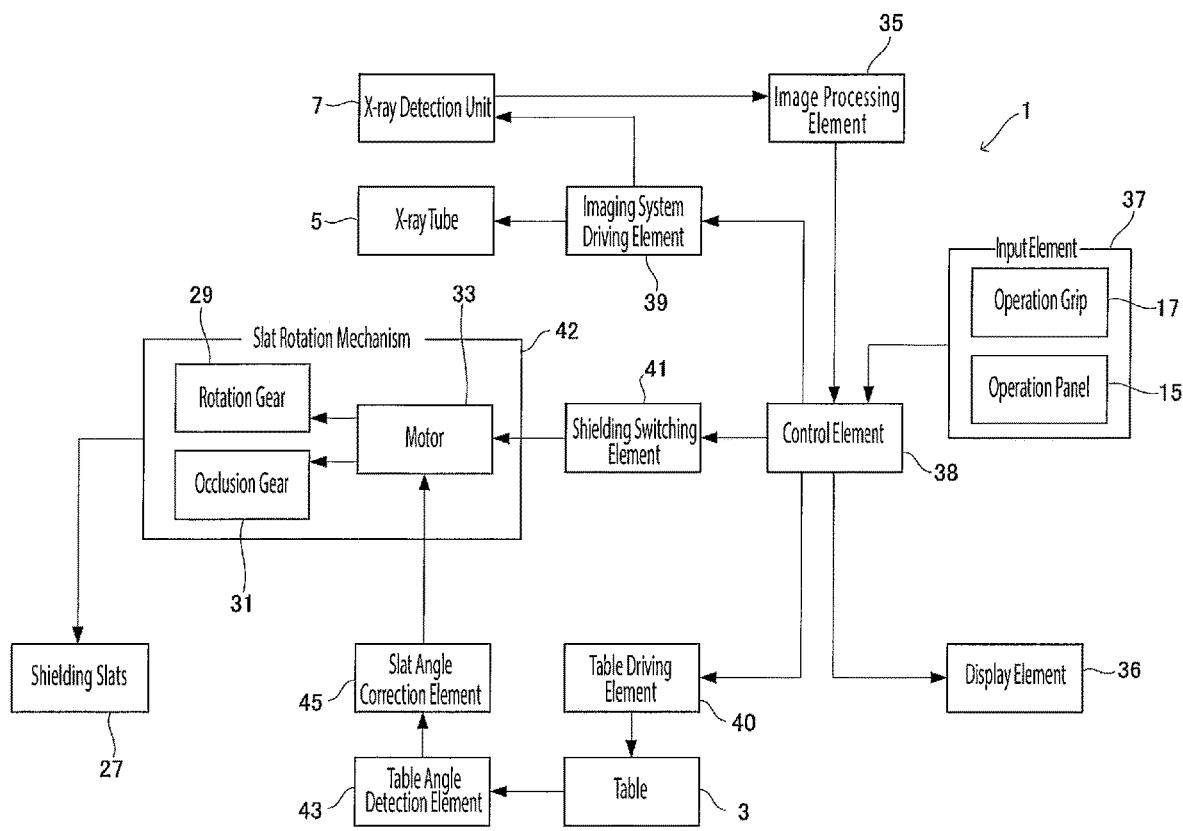
FIG. 5 is a functional block diagram illustrating the proximity operative X-ray fluoroscopic imaging apparatus according to the Embodiment.

The inventors set forth the configuration of the X-ray shielding unit 19. FIG. 3 is the back view of the X-ray shielding unit 19 and FIG. 4 is the plane view of the X-ray shielding unit 19. In addition, the X-ray shielding unit 19 is illustrated in FIG. 1 and FIG. 4 is in the shielding state described later.

The X-ray shielding unit 19 comprises a plurality of pieces of shielding slat 27, a rotation gear 29, an occlusion gear 31 and a motor 33. According to the present Embodiment, the X-ray shielding unit 19 comprises five pieces of shielding slat 27.

The pedestal portion of the respective shielding slats 27 is connected with the end of the X-ray detection unit 7. Specifically, the X-ray detector 8 is indirectly connected with the pedestal portion of the shielding slats 27 through the X-ray detection unit 7. And respective free ends of the shielding slats 27 are extending toward the load surface of the table 3. The plurality of the shielding slats 27 are arrayed in parallel along the long side direction of the table 3. The shielding slats 27 are made of an X-ray shielding (blocking) material and an example of such a component material is lead.

The rotation gears 29 are arrayed and connected with the back plane of the shielding slats 27. The respective shielding slats 27 are connected with the X-ray detection unit 7 through the rotation axis 30 of the rotation gear 29. The respective rotation gears 29 enable to rotate around the axis intersecting to the plane of the shielding slats 27 (X-ray shielding plane). According to the present Embodiment, referring to FIG. 1 and so forth, the respective shielding slats 27 are arrayed in parallel so as to allow the X-ray shielding plane to be orthogonal to the short side direction of the table 3. Specifically, the shielding slats 27 can rotate in synchronism with the rotation of the rotation gear 29 around the axis which is in parallel to the short side direction of the table 3.

The occlusion gears 31 are in place between the respective rotation gears 29 and meshing with each rotation gear 29. Specifically, the X-ray shielding unit 19 of the present Embodiment comprises five rotation gears 29 and four occlusion gears 31. The occlusion gears 31 rotate in the opposite direction to the rotation direction of the rotation gears 29, so that all rotation gears 29 rotates in the same direction.

A motor 33 is directly connected with a rotation axis 30 of at least one rotation gear 29 of a plurality of rotation gears 29. The respective rotation gears 29 rotate in synchronism with one another in the same direction and with the same angle following rotation of the motor 33. And the respective shielding slats 27 rotate in the same direction and with the same angle around the axis intersecting with the X-ray shielding plane. The respective shielding slats 27 rotate, so that the X-ray shielding unit 19 can be switched between the shielding state and the releasing state. The respective shielding slats 27 are arrayed so that the plane of the shielding slat 27 is orthogonal to the short side direction of the table 3. Accordingly, the respective shielding slats 27 rotate around the short side axis of the table 3 following the rotation of the rotation gears 29.

<Control of X-Ray Fluoroscopic Imaging Apparatus>

The X-ray fluoroscopy imaging apparatus 1 further comprises: an image processing element 35; a display element 36; an input element 37; a control element 38; an imaging system driving element 39; a table driving element 40; a shielding switching element 41; a table angle detection element 43; and a slat angle correction element 45.

The image processing element 35 that is installed to the latter part of the X-ray detection unit 7 generates an X-ray image based on the X-ray detection signal output from the X-ray detector 8 of the X-ray detection unit 7. The display element 36 displays the X-ray image and one example thereof is a liquid crystal monitor.

The input element 37 for inputting a variety of instructions by the operator as to an action of the X-ray fluoroscopic imaging apparatus 1 comprises such as the operation panel 15 and the operation grip 17. The control element 38 comprises e.g., a central processing unit (CPU) and so forth, and comprehensively controls the respective components of the X-ray fluoroscopic imaging apparatus 1 in accordance with such as the instruction input into the input element 37 by the operator.

The imaging system driving element 39 moves the X-ray tube 5 and the X-ray detection unit 7 according to the control signal of the control element 38. The imaging system driving element 39 of the present embodiment is configured to allow the X-ray tube 5 and the X-ray detection unit 7 to move in synchronism with each other in the long side and short side direction of the table 3. In addition, the imaging system driving element 39 is configured to allow the X-ray detection unit 7 to move independently from the X-ray tube 5 in the extending direction (z-direction in FIG. 1) of the support column 9.

The table driving element 40 moves the table 3 according to the control signal of the control element 38. Specifically, the table 3 rotates around the parallel axis to the short side direction of the table 3, and the titling angle of the subject M to the horizontal plane can be arbitrary changed. In addition, the table driving element 40 can change the relative position of the table 3 to the imaging system by shifting the table 3 to either x-direction or y-direction.

The shielding switching element 41 switches the X-ray shielding unit 19 between the shielding state and the releasing state according to the control signal of the control element 38. The shielding switching element 41 comprises a slat rotation mechanism 42 having the rotation gears 29, the occlusion gear 31 and the motor 33 rotates the respective shielding slats 27 around the axis parallel to the short side direction of the table 3.

A table angle detection element 43 comprise e.g., a potentiometer or an encoder and detects the tilt angle R1 of the table 3 to the horizontal plane thereby as needed. A slat angle correction element 45 is in place in the latter part of the table angle detection element 43. The slat angle correction element 45 calculates a correction angle R2, with which the respective shielding slats 27 rotate, based on the information as to the tilt angle R1 detected by the table angle detection element 43. The slat angle correction element 45 has also a function to control a slat rotation mechanism 42, so that the rotation angle of the shielding slats 27 becomes the correction angle R2.

<Operation of X-Ray Fluoroscopic Imaging Device>

Now, the inventors illustrate the action of the X-ray fluoroscopic imaging apparatus 1 while describing particularly the operation of the X-ray shielding unit 19.

First, the inventors illustrate the case in which the subject M is being laid in a horizontal state for the X-ray fluoroscopic imaging. First, the operator S rotates the table 3 to be horizontal by operating the input element 37 and loads the subject M on the table 3 in the dorsal position. And the rotation angle of the motor 33 is arbitrary adjusted by operating the input element 37 so that the X-ray shielding unit 19 is in the shielding state.

The shielding state is a state where the X-ray radiation exposure dose to the operator S is reduced in a relatively high efficiency by shielding the space between the operator S and the subject M using the shielding slats 27. When the table in horizontal, the X-ray shielding unit 19 is switched to provide with the shielding state by rotating the respective shielding slats 27 so that the long side direction of the shielding slat 27 is orthogonal to the loading plane of the table 3.

The configuration of the X-ray fluoroscopic imaging apparatus 1 wherein the table 3 is in the horizontal state and the X-ray shielding unit 19 is in the shielding state is shown as-is in FIG. 1 and FIG. 2. The long side of the shielding slats 27 turns to be orthogonal to the loading plane of the table 3, so that an overlapping area of the shielding slats 27 with one another becomes minimum in the front view of the X-ray fluoroscopic imaging apparatus 1. Accordingly, the area of the X-ray shielding plane of the X-ray shielding unit 19 becomes maximum (referring to the sign P1).

Following switching the shielding unit 19 into the shielding state, the operator S adjusts the position of the imaging system using the operation panel 15 and the operation grip 17 and so forth and also sets up an X-ray irradiation condition such as a tube voltage and a tube electric current. And then, the operator generates the X-ray image by irradiating X-rays from the X-ray tube 5 while providing the instruction with the subject M. At this time, referring to FIG. 2, the X-ray shielding unit 19 is in the shielding state, so that the respective shielding slats 27 shield adequately the space between the X-ray fluoroscopic imaging apparatus 1 and the operator S. Accordingly, the X-ray dose irradiated from the X-ray tube 5 and exposed to the operator S can be efficiently reduced.

Second, the inventors illustrate the case in which the X-ray shielding unit 19 is switched to the releasing state while the subject M is being laid in a horizontal position. Once the X-ray shielding unit 19 is turned into the shielding state, the sight of the operator S is blocked by the shielding slats 27, so that it becomes difficult to recognize visually the subject M, particularly. Therefore, for example, when the operator S would not be exposed to the radiation and the necessity to recognize visually the table 3 or the subject M and so forth is high, the action can be performed more smoothly by releasing the shielding state of the X-ray shielding unit 19.

When switching the X-ray shielding unit 19 into the releasing state, the operator S adjusts arbitrary the rotation angle of the motor 33 by operating the input element 37. The releasing state is the state in which the shielding state of the X-ray shielding is released, and it is the state in which the space between the operator S and the subject M is not shielded by the shielding slats 27. In other words, it is the state in which the sight of the operator S is not blocked by the shielding slats 27.

According to the present Embodiment, the X-ray shielding unit 19 is switched from the shielding state to the releasing state by adjusting the rotation angle of the motor 33 so that the respective shielding slats 27 rotates to the 90° left (i.e., counterclockwise rotation). The motor 33 rotates, so that the rotation gears 29 directly connected with the motor 33 rotes counterclockwise. A rotation force of such a rotation gear 29 is transferred to another rotation gear 29 through the occlusion gear 31 and the rotation gears 29 rotate respectively counterclockwise in synchronism with one another.

Figure 6:
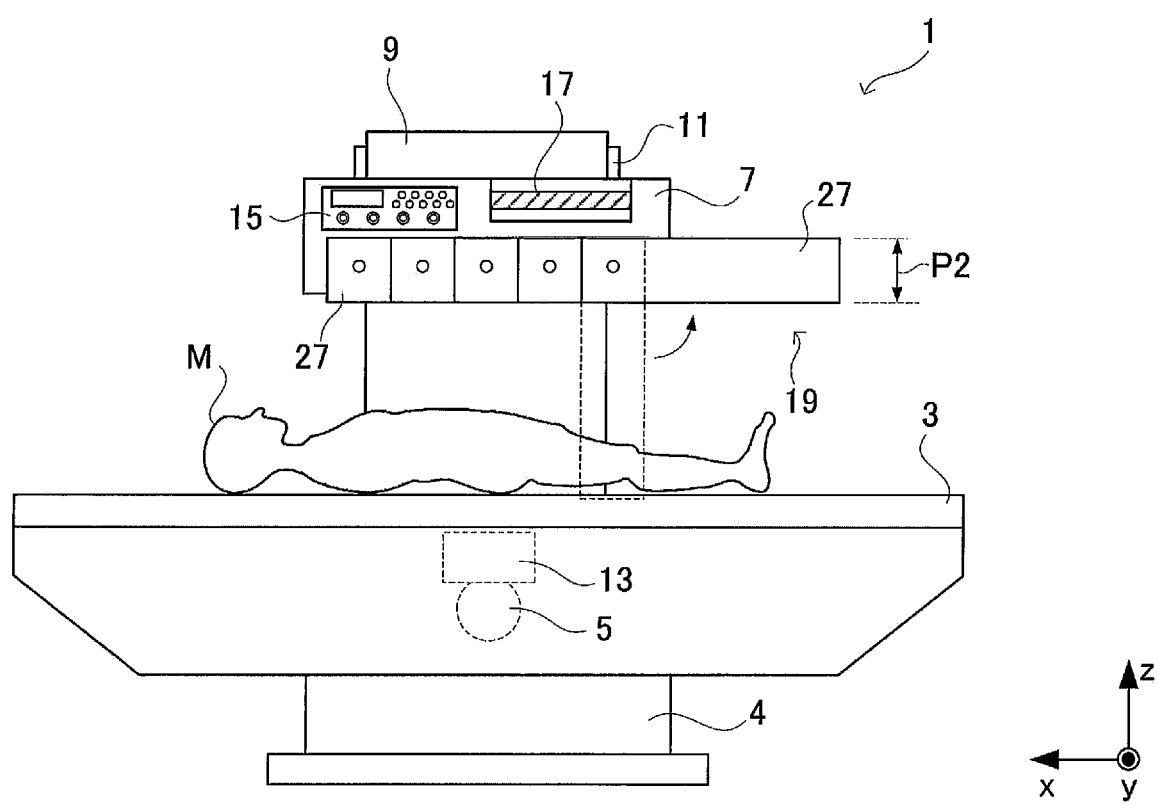
FIG. 6 is a front view illustrating the releasing state relative to the proximity operative X-ray fluoroscopic imaging apparatus according to the Embodiment.
Figure 7:
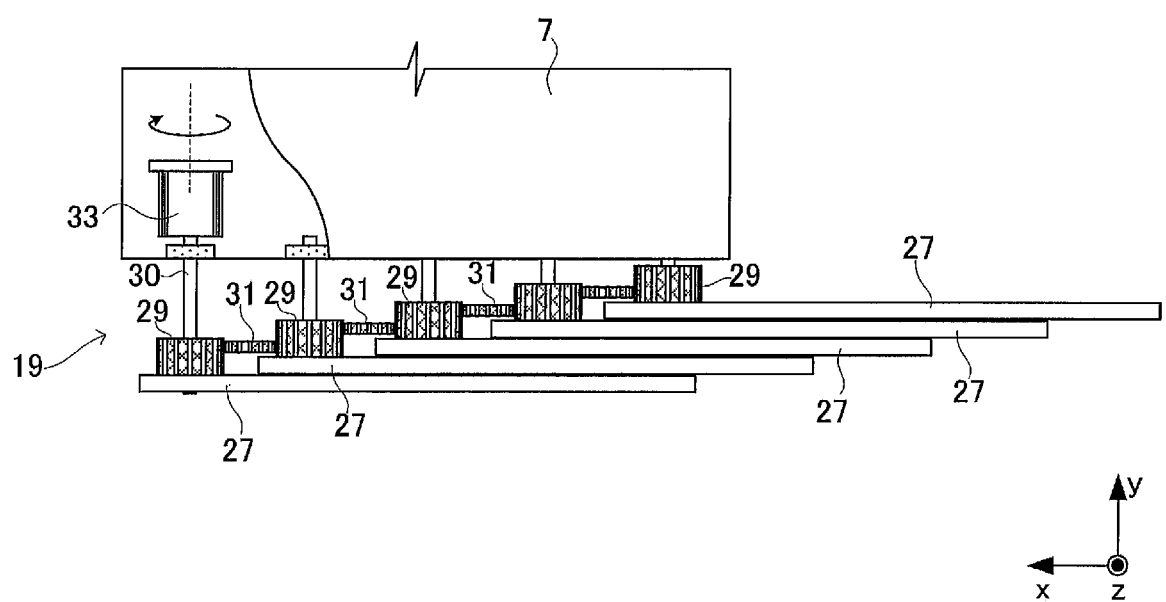
FIG. 7 is a plan view illustrating the structure of the X-ray shielding unit in the releasing state according relative to proximity operative X-ray fluoroscopic imaging apparatus according to the Embodiment.

The rotation gears 29 rotate respectively, so that the respective shielding slats 27 rotate 90° counterclockwise. Referring to FIG. 6 and FIG. 7, the long side direction of the respective shielding slats 27 become parallel to the loading plane of the table 3 along with the rotation of such shielding slats 27. And the short side direction of shielding slats 27 are orthogonal to the loading plane of the table 3. As a result, the respective shielding slats 27 are overlapped with one another in the front view of the X-ray fluoroscopic imaging apparatus 1. Therefore, the area of the X-ray shielding plane of the X-ray shielding unit 19 becomes minimum (referring to the sign P2). The switching operation into the releasing state is completed by narrowing the X-ray shielding plane of the X-ray shielding unit 19. In addition, referring to FIG. 6, for convenience's sake to illustrate, the right end position of the shielding slats 27 in the shielding state is denoted by the dotted line.

When the X-ray shielding unit 19 is switched from the shielding state to the releasing state, the X-ray shielding area is minimum and also the shielding slats 27 are overlapped with the X-ray detection unit 7 in the front view of the X-ray fluoroscopic imaging apparatus 1. Accordingly, the operator S sight relative to the loading plane of the table 3 cannot be blocked with the X-ray shielding unit 19 by switching the units 19 into the releasing state. The operator S puts the X-ray shielding unit 19 into the releasing state, so that the subject M on the table 3 can be easily and visually recognized and as a result, the posture of the subject M can be more adequately adjusted.

In such a way, the X-ray shielding unit 19 of the present invention rotates the respective shielding slats 27 connected with X-ray detection unit 7 around the short side direction of the table 3, so that the shielding state can be switched to the releasing state. Specifically, the state of the X-ray shielding unit 19 can be switched while keeping the connected condition in which the X-ray shielding slats 27 is being connected with the X-ray detection unit 7, so that the X-ray shielding unit 19 can be switched from the shielding state to the releasing state without taking the X-ray shielding unit 19, having the X-ray shielding slats 27, off the X-ray fluoroscopic imaging apparatus 1.

In addition, the respective shielding slats 27 rotate and shift around the pedestal end supported by the X-ray detection unit 7 as the center thereof, so that the shielding state can be switched from the shielding sate to the releasing state. Specifically, when switching to the releasing state, the positional relationship between the X-ray detection unit 7 and the shielding slats 27 does not change, so that the weight balance of the X-ray shielding unit 19 acting on the X-ray detection unit 7 can be kept always constant. Accordingly, an incident of dislocation or angle distortion of the X-ray detector 8 due to the change of the weight balance relative to the X-ray detection unit 7 when switching between the shielding state and the releasing state can be prevented.

Once preparation for irradiating X-ray while adjusting the posture of the subject M is completed, the operator S adjusts the rotation angle of the motor 33 to rotate the shielding slats 27 90° to the right (clockwise) by operating the input element 37. According to such a rotation, the X-ray shielding unit 19 is switched from the releasing state, in which the area of the X-ray shielding plane is minimum, to the shielding state, in which the area of the X-ray shielding plane is maximum. The X-ray exposed dose against the operator S when the X-ray is irradiated can be reduced by switching to the shielding state.

Third, the inventors illustrate the case in which the subject M is being in a tilting position for the X-ray fluoroscopic imaging. In the medical diagnosis of the digestive tract e.g., stomach, the X-ray image, in some case, imaging the subject M in the tilting position may be needed in addition to the image imaging the subject M in the horizontal position Then, the operator S puts the X-ray shielding unit 19 into the shielding state following completion of preparation for the X-ray irradiation. And the input element 37 is operated to rotate the table 3 around the axis parallel to the y-direction (referring to the sign F).

Figure 8:
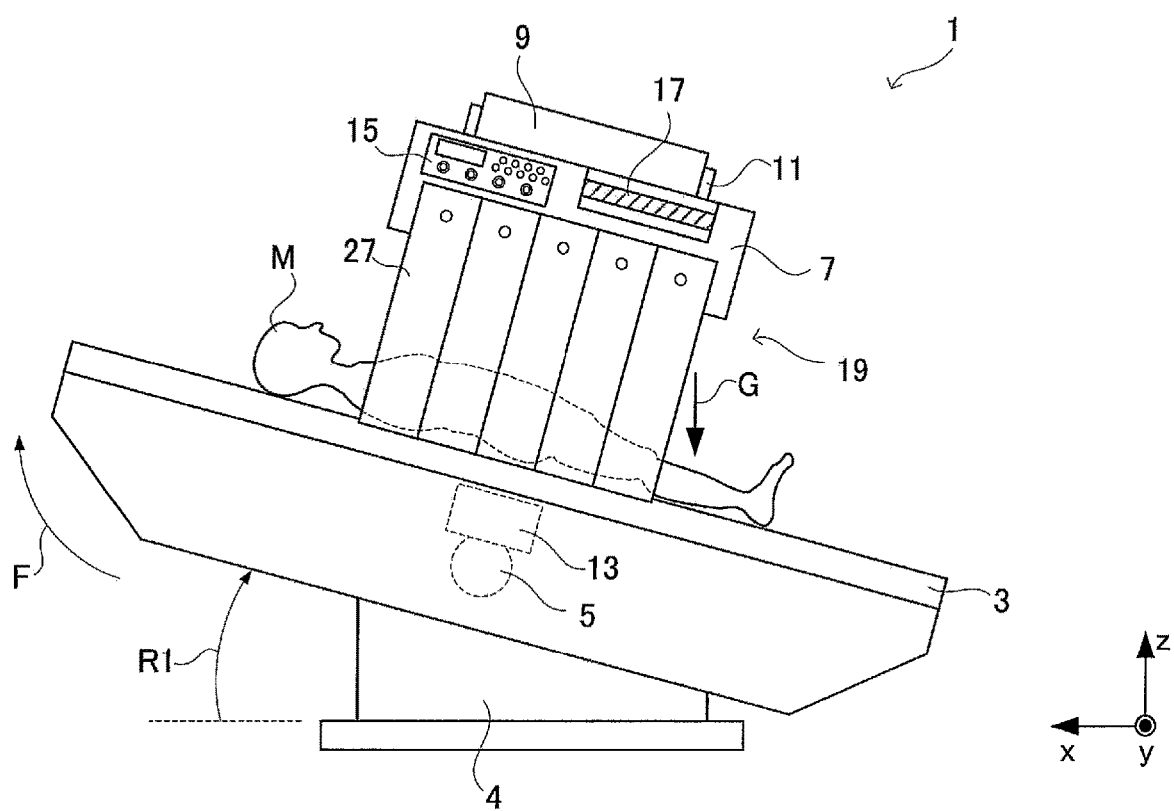
FIG. 8 is a front view illustrating the structure when the table of the proximity operative X-ray fluoroscopic imaging apparatus according to the aspect of the Embodiment is being tilted.
Figure 9:
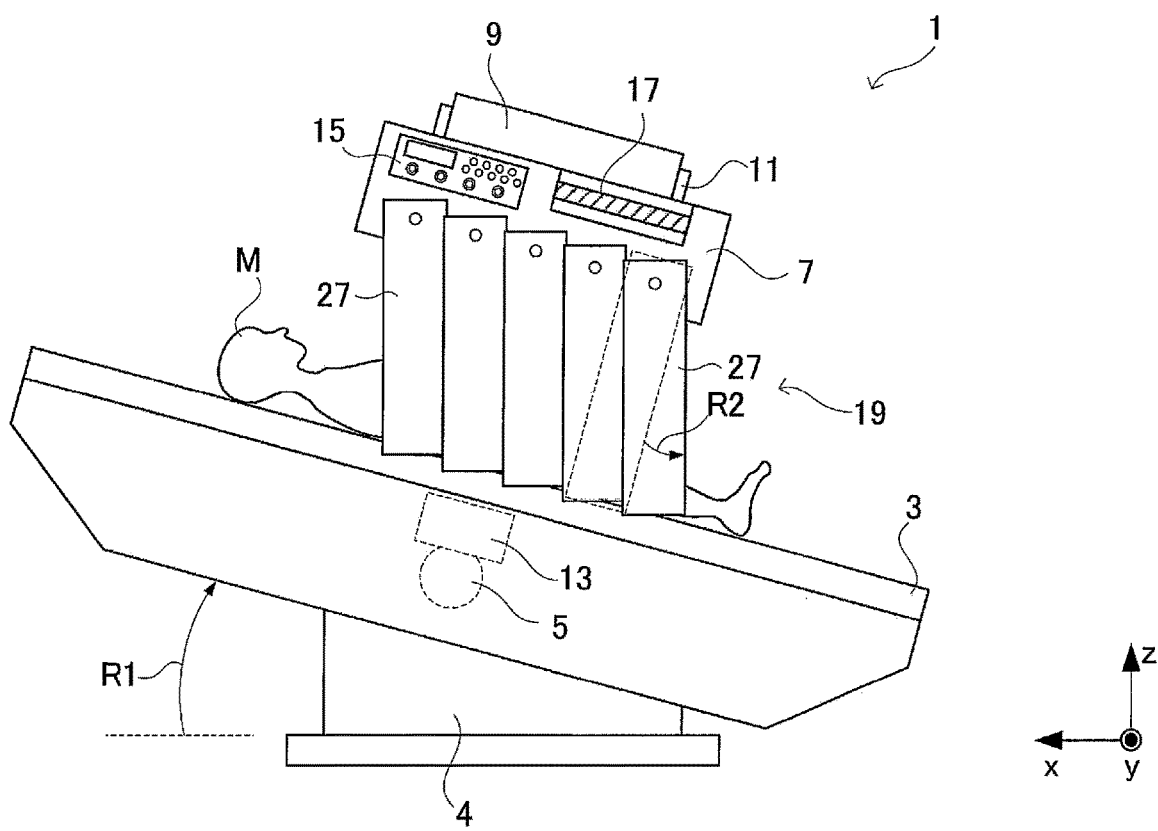
FIG. 9 is a front view illustrating the structure when the table of the proximity operative X-ray fluoroscopic imaging apparatus according to the Embodiment is tilted and the angle of the shielding slats is corrected.
Figure 10:
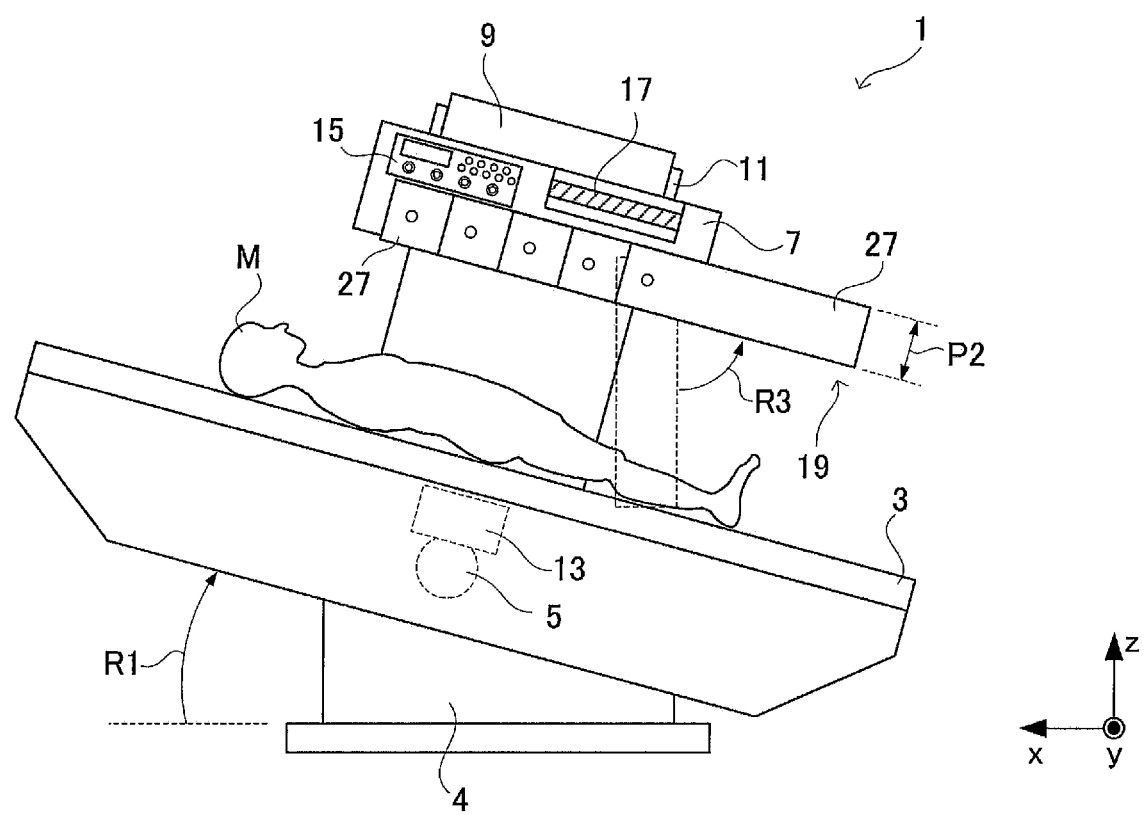
FIG. 10 is a front view illustrating the structure of the proximity operative X-ray fluoroscopic imaging apparatus of the Embodiment of which the table is tilted, and the shielding unit is switched from the X-ray shielding state to the releasing state.

The horizontal state of the table 3 referring to FIG. 1 shifts to the tilting state referring to FIG. 8 and FIG. 10, i.e., tilting to the horizontal plane by rotating the table 3. Now, according to the rotation of the table 3, the components connected with the table 3, i.e., such as the support column 9, the X-ray tube 5 and the X-ray detection unit 7, shift into the tilting state together with the table 3. In addition, FIG. 8 and FIG. 9 show the structure of which the X-ray shielding unit 19 is switched into the shielding state.

Referring to such as FIG. 1, the shielding slats 27 are connected with the X-ray detection unit 7. Accordingly, unless the angle of the shielding slat 27 in the tilting state of the table 3 is corrected particularly, the respective shielding slats 27 tilt relative to the horizontal plane in synchronism with the rotation of the table 3, referring to FIG. 8.

Generally, the shielding slats 27 are made of the sheet material including e.g., lead to have a flexibility but relatively heavy. Accordingly, when the long side of the shielding slats 27 tilt largely relative to the horizontal plane, the shielding slats 27 may deform as distorted in the vertical direction due to the own weight denoted by the sign G. Such a distortion occurred in the shielding slats 27 remains even after the table 3 returns into the horizontal position and it can be a cause of functional deterioration of the X-ray shielding unit 19 in a long time.

Therefore, when titling the table 3 into the tilting state by rotating according to the present Embodiment, a further corrective action of the angle of the shielding slats 27 is preferably performed to avoid the deformation of the shielding slats 27 from a configuration standpoint. Specifically, the X-ray fluoroscopic imaging apparatus 1 comprises the table angle detection element 43 and the slat angle correction element 45. And the tilt angle R1 between the loading plane of the table 3 and the horizontal plane is detected by the table angle detection element 43 as needed. The information relative to the tilt angle R1 is sent from the table angle detection element 43 to the slat angle correction element 45.

The slat angle correction element 45 calculates a correction angle R2 of the shielding slats 27 using the information as to the tilt angle R1 of the table 3. The correction angle R2 is calculated as the rotation angles of the respective shielding slats 27 not to cause distortion on the shielding slats 27 even if the table 3 tilts. The slat angle correction element 45 controls the rotation angle of the motor 33 to provide the rotation angles of the respective shielding slats 27 having the correction angle R2 following the calculation of the correction angle R2. Referring to FIG. 9, according to the control result provided by the slat angle correction element 45, the facing direction of the shielding slats 27 can be adjusted into the direction in which no distortion on the shielding slats 27 takes place.

Specifically, the slat angle correction element 45 of the present embodiment calculates the correction angle R2 of the shielding slats 27 as the angle equal to as the tilt angle R1 of the table 3. When the tilt angle R1 is equal to the correction angle R2, the long side direction of the shielding slats 27, i.e., the direction in which the free ends of the shielding slats 27 are extending, is parallel to the perpendicular direction. Accordingly, not only the X-ray toward the operator S can be efficiently shielded, but also the incident in which the shielding slats 27 deform due to the own weight can be further absolutely prevented.

In addition, when the X-ray shielding unit 19 is switched from shielding state to the releasing state under the condition in which the tilt angle of the table 3 to relative to the horizontal plane is R1, the shielding switching element 41 adjusts the rotation angle of the motor 33 so that the rotation angle of the respective shielding slats 27 is R3. According to the present Embodiment, a value of the rotation angle R3 is obtained based on the tilt angle R1 using the following formula (A) as the preferred method for calculating the value of the rotation angle R3.

$$R3=(90°-R1) \quad (A)$$

Referring to FIG. 10, the shielding slats 27 are rotated to provide the rotation angle of the shielding slat 27 having R3 obtained using the above formula (A), so that the long side direction of the respective shielding slats 27 become parallel to the loading plane of the table 3. And the respective shielding slats 27 are overlapped with one another in the front view of the X-ray fluoroscopic imaging apparatus 1. Therefore, the area of the X-ray shielding plane of the X-ray shielding unit 19 can be minimized (referring to the sign P2). Accordingly, the sight of the operator S becomes further wider relative to the table 3 and the subject M.

Effects of the Aspect of the Embodiment

According to the present Embodiment, a proximity operative X-ray fluoroscopic imaging apparatus 1 comprises: a table 3 on which a subject M is held; an imaging system in which an X-ray tube 5 that irradiates X-ray and an X-ray detector 8 that detects the X-ray irradiated from the X-ray tube 5 and transmitting a subject M are facing each other while sandwiching the table 3; a table driving element 40 that tilts the table relative to the horizontal plane; an X-ray shielding unit 19 that is supported so as to be freely rotatable by the imaging system having a plurality of X-ray shielding slats 27, wherein each pedestal end of the X-ray shielding slats 27 is in place above the table 3 and each free end of the shielding slats 27 is extending toward the loading surface of the table and the plurality of the shielding slats 27 are arrayed in parallel along the long side of the table 3; and a switching element 41 that switches the shielding state, where the X-ray shielding unit 19 is placed in between the subject M and the operator S to block the X-ray exposure to the operator S, and the releasing state; wherein the shielding switching element 41 further comprises: the slat rotation mechanism 42 that rotates the respective shielding slats 27 around the short side direction axis of the table 3, wherein the slat rotation mechanism 42 rotates the shielding slats 27 to switch between the shielding state and the releasing state.

According to such a configuration, the X-ray shielding unit 19 can be switched between the shielding state and the releasing state without taking the X-ray shielding unit 19 having the shielding slats 27 off the X-ray fluoroscopic imaging apparatus 1. Accordingly, the weight balance of the X-ray imaging system would not change even when the X-ray shielding unit 19 is switched to the releasing state, so that the incident of lowering the operability of the proximity X-ray fluoroscopic imaging apparatus can be avoided. In addition, the action to connect the dummy weight with the X-ray detection unit 7 when the shielding state and the releasing state are switched is not needed, so that the workload on the operator lowers and the convenience of the X-ray fluoroscopic imaging apparatus 1 is improved.

In addition, according to the present Embodiment, the slat rotation mechanism 42 changes the rotation angle of shielding slats 27 corresponding to the angle generated by the table driving element 40 to tilt the table 3. In such a configuration, the shielding slats 27 can be rotated arbitrary corresponding to the tilt angle R1 of the table 3 when the table driving element 40 tilts the table 3 relative to the horizontal plane. Accordingly, the incident of deformation of the X-ray shielding slats 27 due to the own weight of the X-ray shielding unit 19 can be avoided.

In addition, according to the present Embodiment, the slat rotation element 42 switches from the shielding state to the releasing state by rotating the respective shielding slats 27 so that the traveling direction of the free end of the shielding slats 27 becomes in parallel to the long side direction of the table 3. In such a configuration, the X-ray shielding plane of the X-ray shielding unit 19 that is changed to the releasing state becomes narrower. Accordingly, the operator sight for such as the loading plane of the table 3 can be ensured more adequately when the X-ray shielding unit 19 is switched to the releasing state.

Other Embodiments

Specifically, the aspects of the Embodiment disclosed at this time are examples and not limited thereto in any points. The scope of the present invention is specified in the claims and all alternatives are included in the scope of the claims and equivalents thereof. For example, the present invention can be implemented in the below alternative Embodiment.

(1) According to the present invention set forth above, the X-ray shielding unit 19 comprises the plurality of shielding slats 27 that are arrayed in parallel along the long side direction of the table 3, but the present invention is not limited thereto. Specifically, the direction in which the shielding slats 27 are arrayed in parallel and the position where the shielding slats 27 are in place may be arbitrary changed, corresponding to the positional relationship between the operator S and the X-ray fluoroscopic imaging apparatus 1 when the operator S operates the X-ray fluoroscopic imaging apparatus 1.

(2) According to the present invention set forth above, the slat rotation mechanism 42 comprises one motor 33, a plurality of the rotation gears 29 and the occlusion gear 31, but the structure of the slat rotation mechanism 42 is not limited to the present embodiment as long as the structure in which the shielding slats 27 rotate. As the other embodiment of the slat rotation mechanism 42, each motor 33 is connected in series with each rotation axis 30 of the respective shielding slats 27 and a plurality of the respective motors 33 are rotated in synchronism with one another to rotate the respective shielding slats 27.

In addition, the configuration wherein the slat rotation mechanism 42 rotates automatically the shielding slats 27 using such as the motor 33 is not limited thereto and the shielding slats 27 can be rotated manually. One example of such as the manual rotation may be the configuration in which the slat rotation mechanism 42 may comprise only the rotation gears 29 and the occlusion gear 31. Specifically, the operator S rotates manually the shielding slats 27 while holding one of the shielding slats 27, so that the rotation force of the shielding slat 27 being held can be transferred to all shielding slats 27 through the rotation gears 29 and the occlusion gear 31. As results, all shielding slats 27 can be rotated manually in synchronism with one another.

(3) According to the present invention set forth above, the table angle detection element 43 that detects the tilt angle R1 of the table 3 if needed, according to the configuration in which the angle of the shielding slats 27 in the shielding state is corrected when the table 3 is tilted relative to the horizontal plane, but the embodiment is not limited thereto. The other embodiment to correct the angle of the shielding slats 27 may be the configuration in which the tilt angle storing element instead of the table angle detection element 43 is included to memorize the information as to the tilt angle R1 of the table 3 which the operator S inputs the input element 37.

According to the present Embodiment, when the operator S performs an operation to tilt the table 3, the information of the tilt angle R1 of the table 3 input by the operator S is sent from the tilt angle storage element to the slat angle correction element 45 through the control element 38, and then the slat angle correction element 45 rotates arbitrary the shielding slats 27 based on the information of the tilt angle R1, so that the angles of the shielding slats 27 can be corrected as the free ends of the shielding slats 27 face in the perpendicular direction.

(4) According to the present invention set forth above, the value of the rotation angle R3 of the shielding slats 27 when switching the shielding state to the releasing state is not limited to the value obtained by the above formula (A) and can be arbitrary set up to the other value. Specifically, the rotation angle R3 can be calculated using the calculation formula different from the above formula (A). In addition, the tilt angle of the table 3 relative to the horizontal plane can be set the rotation angle R3 to be e.g., 90° regardless the degree of the tilt angle of the table 3.

(5) According to the present invention set forth above, the X-ray detector 8 in the imaging system is installed above the table 3, but it is not limited thereto and the X-ray tube 5 of the imaging system may be installed above the table 3. When the X-ray tube 5 is installed above the table 3, the X-ray shielding unit 19 is supported by the X-ray tube 5 or the member embedding with the X-ray tube 5.

REFERENCE OF SIGNS

1 X-ray fluoroscopy imaging apparatus
3 Table
5 X-ray tube
7 X-ray detection unit
8 X-ray detector
15 Operation panel
17 Operation grip
19 X-ray shielding unit
27 Shielding slat
29 Rotation gear
31 Occlusion gear
33 Motor
37 Input element
38 Control element
39 Imaging system driving element
40 Table driving element
41 Shielding switching element
42 Slat rotation mechanism
43 Table angle detection element
45 Slat angle correction element Although only a few embodiments have been disclosed in detail above, other embodiments are possible, and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art of x-ray imaging devices and the complex arrangements therein, including electronics engineers, software engineers, circuit design engineers and related individuals having advanced technical degrees, and as a result basic component elements will be easily understood by those of such skill in the art.

Also, the inventors intend that only those claims which use the complete words "means for" are intended to be interpreted under 35 USC 112 paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray proximity operative X-ray fluoroscopic imaging apparatus, comprising:
    a table on which a subject is held;
    an imaging system further comprising:
        an X-ray tube that irradiates X-ray; and an X-ray detector that detects said X-ray irradiated from said X-ray tube and transmitting said subject, wherein said X-ray tube and said X-ray detector are facing each other and sandwiching said table;
    a table driving element that tilts said table relative to a horizontal plane;
    an X-ray shielding mechanism having a plurality of X-ray shielding slats, wherein each pedestal end of said shielding slats is supported so as to be freely movable with said imaging system that is in place above said table, each free end of said shielding slats is extending toward a loading surface of said table, and said plurality of said shielding slats are arrayed in parallel along a long side of said table;
    a shielding switching element that switches between a shielding state, in which said X-ray shielding mechanism is in place between said subject and an operator to shield an X-ray exposed dose for said operator, and a releasing state, in which said shielding mechanism is being released;
    wherein said shielding switching element further comprises:
        a slat rotation element that rotates said respective X-ray shielding slats around a short side axis of said table and switches between said shielding state and said release state by rotating said respective X-ray shielding slats using said slat rotation element; and
        said slat rotation element changes a rotation angle of said X-ray shielding slats corresponding to an angle generated when said table driving element tilts said table.

2. The proximity operative X-ray imaging apparatus according to claim 1, wherein:
    said slat rotation element switches between said shielding state and said releasing state by rotating said respective X-ray shielding slats so that a traveling direction of said free end of said X-ray shielding slats becomes in parallel to a long side direction of said table.

* * * * *